United States Patent [19]
Dixon et al.

[11] Patent Number: 5,272,154
[45] Date of Patent: Dec. 21, 1993

[54] 3,7 SUBSTITUTED INDOLE AND INDAZOLE COMPOUNDS AND PHARMACEUTICAL COMPOSITIONS CONTAINING THEM

[75] Inventors: Arnold K. Dixon, Wabern; Rudolf K. A. Giger, Muttenz, both of Switzerland

[73] Assignee: Sandoz Ltd., Basel, Switzerland

[21] Appl. No.: 809,815

[22] Filed: Dec. 18, 1991

[30] Foreign Application Priority Data

Dec. 18, 1990 [GB] United Kingdom ............... 9027424
Dec. 18, 1990 [GB] United Kingdom ............... 9027425
Jun. 24, 1991 [GB] United Kingdom ............... 9113596

[51] Int. Cl.$^5$ ........................................... C07D 451/12
[52] U.S. Cl. ..................................... 514/299; 546/112
[58] Field of Search ......................... 546/112; 514/299

[56] References Cited

U.S. PATENT DOCUMENTS

| | | | |
|---|---|---|---|
| 4,789,673 | 12/1988 | Donatsch et al. | 514/214 |
| 4,822,881 | 4/1989 | Coates et al. | 540/603 |
| 4,859,662 | 8/1989 | Coates et al. | 548/336 |
| 4,883,803 | 11/1989 | Tyers | 514/304 |
| 4,985,437 | 1/1991 | Tyers | 514/304 |
| 5,034,398 | 6/1991 | King | 548/371 |

FOREIGN PATENT DOCUMENTS

| | | | |
|---|---|---|---|
| 189002 | 7/1986 | European Pat. Off. | 546/200 |
| 200444 | 11/1986 | European Pat. Off. | 548/336 |
| 261964 | 3/1988 | European Pat. Off. | 548/426 |
| 278173 | 8/1988 | European Pat. Off. | 548/426 |
| 279512 | 8/1988 | European Pat. Off. | 548/336 |
| 307145 | 3/1989 | European Pat. Off. | 548/336 |
| 317088 | 5/1989 | European Pat. Off. | 548/330 |
| 338650 | 10/1989 | European Pat. Off. | 548/336 |
| 339959 | 11/1989 | European Pat. Off. | 548/330 |
| 347229 | 12/1989 | European Pat. Off. | 548/426 |
| 353983 | 2/1990 | European Pat. Off. | 548/330 |
| 373061 | 6/1990 | European Pat. Off. | 548/330 |
| 385722 | 9/1990 | European Pat. Off. | 548/330 |
| 393766 | 10/1990 | European Pat. Off. | 548/336 |
| 89/04660 | 6/1989 | PCT Int'l Appl. | 548/336 |
| 91/01316 | 2/1991 | PCT Int'l Appl. | 548/426 |
| 2193633 | 2/1988 | United Kingdom | 548/336 |

OTHER PUBLICATIONS

Chemical Abstracts, vol. 112, No. 23, Abstract No. 216,686g, p. 519 (Jun. 4, 1990).
Mol. Toxicol., vol. 1, pp. 341-350 (1987).
Eur. J. Cancer Clin. Oncol., vol. 25, Suppl. 1, pp. S75-S77 (1989).

Primary Examiner—G. Warren Ivy
Assistant Examiner—Zinna N. Davis
Attorney, Agent, or Firm—Robert S. Honor; Melvyn M. Kassenoff; Joseph J. Borovian

[57] ABSTRACT 3,7-disubstituted indole derivatives of formula I

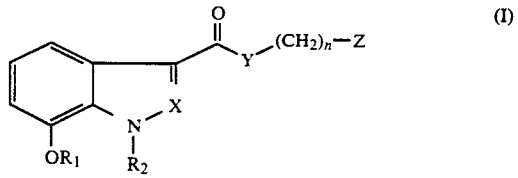

wherein $R_1$, $R_2$, n, X, Y and Z are as defined in the description are useful for the treatment of psychiatric disorders.

5 Claims, No Drawings

3,7 SUBSTITUTED INDOLE AND INDAZOLE COMPOUNDS AND PHARMACEUTICAL COMPOSITIONS CONTAINING THEM

The present invention relates to 3,7-disubstituted indole derivatives, their production, their use as pharmaceuticals and pharmaceutical compositions containing them.

More particularly the present invention provides a compound of formula I

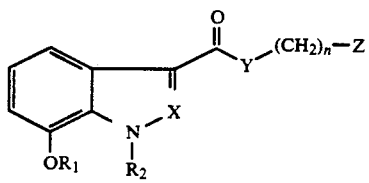

wherein
either $R_1$ is alkyl(1-4C), and
$R_2$ is hydrogen, alkyl(1-7C), alkenyl(3-6C), alkynyl(3-10C), cycloalkyl(3-7C), cycloalkyl(3-7C)alkyl(1-4C), phenyl, phenylalkyl(1-3C), alkyl(1-6C)carbonyl, alkyl(1-6C)oxycarbonyl, carbamoyl, sulfamoyl or mono- or dialkyl(1-6C)carbamoyl or -sulfamoyl,
X is CH or N and
Y is $NR_3$ or O, $R_3$ being hydrogen or alkyl(1-6C), or
X+Y together are C-A-N or C-A-CH, wherein A is CH=CH or —(CH$_2$)$_m$—, being 2 or 3,
n is 0, 1 or 2 and
Z is a group of formula (a)

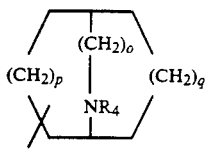

wherein
o is 0, p is 0, 1 or 2 and q is 0, 1 or 2, or
o is 1, p is 0 and q is 0 or 1, and
$R_4$ is hydrogen, alkyl(1-7C), cycloalkyl(3-6C), phenylalkyl(1-4C) optionally mono- or disubstituted by halogen, alkyl(1-4C) or alkoxy(1-4C),
or a group of formula (b)

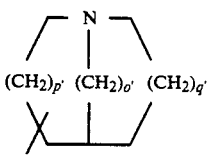

wherein o' is 1, 2 or 3, p' is 0 or 1 and q' is 0 or 1, or a group of formula (c) or (d)

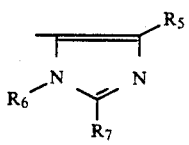

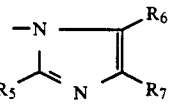

wherein one of $R_5$, $R_6$ and $R_7$ is hydrogen, alkyl(1-6C), cycloalkyl(3-7C), alkenyl(2-6C), phenyl or phenylalkyl(1-3C) and the 2 others independently are hydrogen or alkyl(1-6C), provided that Z is not (d) when n is 0 and Y is $NR_3$ or (with X) N-A-C, or $R_1$ is hydrogen, $R_2$, X, Y and n are as defined above and Z is as defined above but not a group of formula (a) when X is N, in free form or in pharmaceutically acceptable salt or complex form, for use as pharmaceutical.

$R_1$ is preferably alkyl, more preferably methyl.
$R_2$ is preferably hydrogen or alkyl(1-7C).

In $R_2$, alkyl(1-7C) is preferably alkyl(1-4C), more preferably methyl, alkenyl(3-6C) is preferably alkenyl(3-4C), alkynyl(3-10C) is preferably alkynyl(3-4C), cycloalkyl(3-7C) is preferably cycloalkyl(3-6C), cycloalkyl(3-7C)alkyl(1-4C) is preferably cycloalkyl(3-6C)methyl, phenylalkyl(1-3C) is preferably benzyl, alkyl(1-6C)carbonyl is preferably alkyl(1-4C)carbonyl, alkyl(1-6C)oxycarbonyl is preferably alkyl(1-4C)oxycarbonyl and dialkyl(1-6C)carbamoyl and -sulfamoyl are preferably dimethylcarbamoyl and -sulfamoyl.

$R_3$ is preferably hydrogen or methyl.
$R_4$ in (a) is preferably hydrogen or alkyl(1-4C), more preferably methyl.

Preferably one of $R_5$, $R_6$ and $R_7$ in (c) and (d) is methyl and the two others are hydrogen. More preferably $R_5$ is methyl and $R_6$ and $R_7$ are hydrogen.

When X+Y together are C—(CH$_2$)$_m$—CH, m is preferably 0.

In (a) preferably o is 0 and p and q are 1 or p is 1 and q is 2.

When Z is of formula (a) or (b), n is preferably 0. When Z is of formula (c) or (d), n is preferably 1.

In a group of compounds of formula I, $R_1$ is alkyl(1-4C), $R_2$ is hydrogen, X is CH, Y is O or NH, n is 0 and Z is of formula (a')

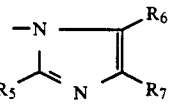

wherein $R'_4$ is methyl, ethyl or propyl and q'' is 0, 1 or 2.

Depending on the nature of the substituents defined above, asymmetric carbons may be present in the molecule. This is the case for example when X+Y together are C-A-CH. All optical isomers and their mixtures including the racemic mixtures are part of the present invention.

Furthermore depending on the nature of the Y—(CH$_2$)$_n$—Z group, the compounds may be present in either the exo or endo configuration. The exo/endo nomenclature is well known in the literature. Again, both exo and endo form and their mixtures are part of the present invention. The endo isomers are preferred.

The compounds of formula I may exist in free form or in salt form. Suitable salt forms include acid addition salts and quaternary ammonium salts.

The compounds of formula I may be prepared by a process comprising a) for the production of a compound of formula Ia

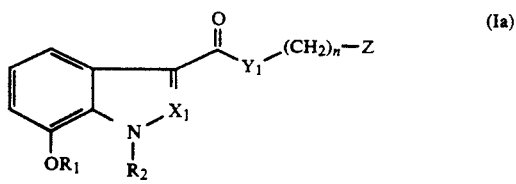

wherein $R_1$, $R_2$, n and Z are as defined above, $X_1$ is CH or N and $Y_1$ is $NR_3$ or O, $R_3$ being as defined above, condensing a compound of formula II

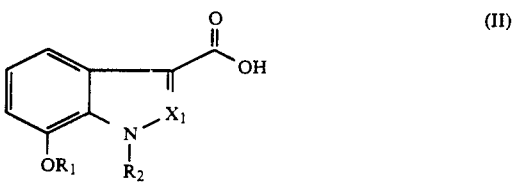

wherein $R_1$, $R_2$ and $X_1$ are as defined above, or a reactive derivative thereof, with a compound of formula III

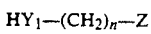

$$HY_1-(CH_2)_n-Z$$

wherein n, Z and $Y_1$ are as defined above, or b) for the production of a compound of formula Ib

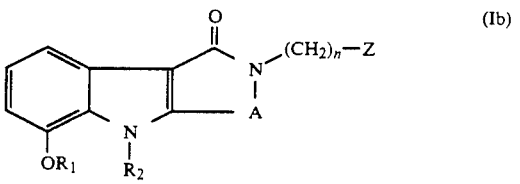

wherein $R_1$, $R_2$, A, n and Z are as defined above, alkylating a compound of formula IV

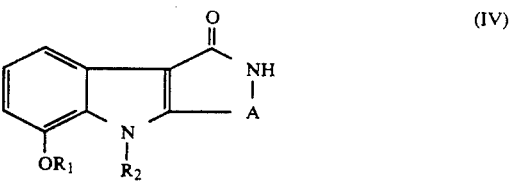

wherein $R_1$, $R_2$ and A are as defined above, with a compound of formula V

$$B-(CH_2)_n-Z \quad (V)$$

wherein n and Z are as defined above and B is a leaving group, or c) deprotecting any protected form of a compound of formula I to obtain a compound of formula I, and recovering the resulting compound of formula I as such or as an acid addition salt or as a quaternary ammonium salt thereof.

Process step a) to obtain amides or esters may be effected in conventional manner for analogous compounds.

For example the carboxylic acid group may be activated in the form of a reactive acid derivative, especially for the production of amides. Suitable reactive acid derivatives may be formed by reaction with N,N'-carbonyl-diimidazole producing an intermediate carboxylic acid imidazolide, or with N-hydroxy-succinimide. Alternatively an acid halogenide, for example an acid chloride, may be used, e.g. produced by reaction with oxalyl chloride.

For the production of esters, the alcohol (compound of formula III wherein $Y_1$ is O) may be conveniently reacted with a compound of formula II or a reactive derivative thereof. The reaction may be carried out at a temperature between room temperature and 70° C. Conveniently an inert solvent, e.g. ethyl acetate, may be used. The alcohol may also be used e.g. in the form of an alkali metal salt, preferably the lithium salt. Such salts may be produced in conventional manner, e.g. by reaction of n-butyl lithium with the alcohol in tetrahydrofuran. If desired a heterocyclic or tertiary amine, e.g. pyridine or triethylamine may be present, especially for the production of amides. Suitable reaction temperatures may be from about −10° C. to about 10° C. Other suitable inert organic solvents include e.g. ether or dimethoxyethane.

In these reactions the endo or exo configuration of the $Y_1-(CH_2)_n-Z$ rest is believed to be maintained. The compound of formula III may be reacted if desired as a mixture of endo and exo isomers and the pure endo or exo isomer isolated, e.g. by chromatography or crystallization.

The alkylation according to process step b) may be effected in conventional manner for analogous compounds. B is preferably a halogen atom.

The deprotection reaction of process step c) is specifically suitable for the production of compounds with secondary amino groups. Example of a protecting group may be acetyl or benzyl. The protecting group may be removed in analogy with known methods, e.g. by hydrogenation. The hydrogenation may be performed in the presence of palladium on active charcoal at room temperature or at slightly elevated temperature. Suitable solvents include acetic acid, ethyl acetate or ethanol.

The compounds of formula I where X and Y together are C—A—CH may be prepared in a manner known for the synthesis of analogous compounds, e.g., as disclosed in European Patent Application No. 317,088.

The compounds of formula I may be isolated and purified in conventional manner.

Insofar as the production of any starting material is not particularly described herein, it is known or may be produced in analogous manner to known procedures or in analogous manner to that described herein, e.g. the example.

Compounds of formula I in free base form may be converted into salt forms. For example acid addition salts may be produced in conventional manner by reaction with a suitable acid, e.g. hydrochloric acid, malonic acid, hydrobromic acid, maleic acid, malic acid, fumaric acid, oxalic acid and tartaric acid. Quaternary ammonium salts of the compounds of formula I may be produced in conventional manner, e.g. by reaction with methyl iodide.

In the following example all temperatures are in °C and are uncorrected.

EXAMPLE: 7-Methoxy-1H-indol-3-carboxylic acid-(1αH, 5αH)8-methyl-8-aza-bicyclo[3,2,1]oct-3α-yl-ester 19.1 g of 7-methoxy-1H-indol-3-yl carboxylic acid are suspended in 300 ml ethyl acetate. 10 ml oxalyl chloride are then added over 30 minutes at room temperature. The resulting red brown solution is stirred for 3 hours at room temperature and then concentrated to ⅜ of its original volume. A solution of 14 g tropine in 50 ml ethyl acetate is added dropwise thereto at a temperature of about 50°. The resulting mixture is further stirred for 2 hours at about 50° and then over night at room temperature. The resulting suspension is dissolved by addition of water and the mixture is extracted three times with ethyl acetate and then washed with 2N HCl. The acidic phase is alkalized with potassium carbonate, extracted three times with $CH_2Cl_2$ and evaporated, thus yielding the title compound. m.p. 298°-299° (decomposition)

The compounds of formula I in free form or in the form of pharmaceutically acceptable salts and complexes (hereinafter referred to as compounds of the invention) have never been disclosed in the literature as pharmaceuticals. They exhibit valuable pharmacological properties as indicated in animal tests and are therefore indicated for therapy.

In particular, the compounds of the invention show sociotropic activity (A. K. Dixon, et al, Adv. Study. Behav., 1990, 19, 171–204) as indicated e.g. by the intruder test with mice as disclosed by A. K. Dixon, Triangle, 1982, 21, 95–105. In this test, the compounds of the invention have a dose-related increase in approach-oriented social activities after administration at dosages of from about 0.01 to 100 μg/kg. These activities are evident after oral and parenteral administration and affect social investigation (increased) and defensive ambivalence (decreased).

The compounds of the invention also influence social behavior as demonstrated in the test according to K. A. Dixon et al., Adv. Study Behav., 19, 171, (1990) where pairs of individually housed males are brought together in a large cage unfamiliar to them both and their behavioral acts and postures are then recorded. In this test, one partner of a pair receives either the compound to be tested or vehicle i.p. 45 minutes before the social encounter. When administered i.p. at dosages from about 0.01 to 100 μg/kg, the compounds of the invention have effects on the social behavior of the mice, e.g. they increase social investigation.

The compounds of the invention also reduce the plasma corticosterone rise induced in mice by the presence of an aggressive, but inaccessible male mouse. Compounds of the invention when given p.o. for 14 days at a dosage of from about 0.1 to 10 mg/kg restore the plasma corticosterone level to normal.

Furthermore, the compounds of the invention exhibit 5HT$_3$ antagonistic properties as evidenced by:

1. their potent and selective binding properties to 5-HT3 binding sites, e.g. to N1E-115 cells measured according to the method disclosed by D. Hoyer and H. C. Neijt, Mol. Pharm., 33, 303–309. Example compound has a pKd value of 8.87±0.01.

2. their promoting effect on gastric emptying in rats as indicated in standard in vivo tests when administered i.p. at doses of about 0.01 to about 1 mg/kg. The compounds to be tested are administered 15 min. before the administration of 25 glass spheres and gastric emptying is measured 5, 10, 15 and 30 min. after administration of the spheres. Example compound has an ED$_{50}$ of 0.2 mg/kg i.p.

3. their blockade of the Benzold Jarisch Reflex, e.g. as demonstrated in the test method according to J. R. Fozard, Naunyn-Schmiedeberg's Arch. Pharmacol., 326, 36–44 (1984). Example compound has an ID$_{50}$ of 70 μg/kg.

The compounds of the invention are accordingly indicated for treating psychiatric disorders, particularly for the treatment of anxiety of various genesis and of stress-related disorders. The compounds of the invention are also indicated for the treatment of disorders such as social withdrawal, affective disorders, psychoses, depression, cognitive disorders, disorders of vigilance, e.g. geriatric illnesses, panic disorders, agoraphobia, and obsessive compulsive disorders.

For these indications, the appropriate dosage will, of course, vary depending upon, for example, the host, the mode of administration and the severity of the conditions being treated. However, in general, satisfactory results in animals are indicated to be obtained at daily dosages from about 0.1 μg/kg to about 1 mg/kg animal body weight. In larger mammals, for example humans, an indicated daily dosage is in the range from about 0.01 to about 5 mg of the compounds of the invention conveniently administered, for example, in divided doses up to four times a day.

The Example compound is preferred. It has for example been determined that this compound reduces the stress-induced corticosterone concentration in plasma in the above mentioned social stress model when administered p.o. at a dosage of from 0.1 to 1 mg/kg. It is therefore indicated that this compound may be administered at daily dosages of from 0.01 to 5 mg p.o. to larger mammals, for example humans.

The compounds of the invention may be administered in free form or in pharmaceutically acceptable salt or complex form. Such salts may be prepared in conventional manner and exhibit the same order of activity as the free compounds.

The present invention also provides a pharmaceutical composition comprising a compound of the invention in association with a pharmaceutically acceptable diluent or carrier. Such compositions may be formulated in conventional manner. The compounds of the invention may be administered by any conventional route, for example parenterally e.g. in form of injectable solutions or suspensions, enterally, e.g. orally, for example in the form of tablets or capsules or in a nasal or a suppository form. Unit dosage forms contain, for example, from about 2.5 μg to 2.5 mg of a compound of the invention in free form or in pharmaceutically acceptable salt form.

In accordance with the foregoing the present invention furthermore provides a method for treating psychiatric disorders, for example as herein before indicated, e.g. anxiety, stress-related disorders or depression, in a subject in need of such treatment, which method comprises administering to said subject an effective amount of a compound of the invention.

The compounds of formula I in free form or in salt or complex form have never been specifically disclosed in the literature, with the exception of:

7-hydroxy-1H-indol-3-carboxylic acid-(1H,5H)-8-methyl-8-azabicyclo[3,2,1]oct-3-yl-ester which has been mentioned in Mol. Toxicol. 1, 341–350, 1987 as a possible minor metabolite produced in the in vitro metabolism of 1H-indol-3-carboxylic acid-(1H,5H)-8-methyl-8-aza-bicyclo[3,2,1]oct-3-yl-ester by differentiated rat and human hepatoma cells;

1,2,3,9-tetrahydro-8-hydroxy-9-methyl-3-[(2-methyl-1H-imidazol-1-yl)methyl]-4 H-carbazol-4-one which has been mentioned in Eur. J. Cancer Clin. Oncol. 25 (Suppl. 1) 75–77, 1989, as a metabolite of 1,2,3,9-tetrahydro-9-methyl-3-[(2-methyl-1H-imidazol-1-yl)methyl]-4 H-carbazol-4-one.

Thus in yet a further aspect the present invention provides a compound of formula I wherein either $R_1$ is alkyl(1-4C), and $R_2$, X, Y, n and Z are as defined above, or $R_1$ is hydrogen, $R_2$, X, Y and n are as defined above and Z is a group of formula (b) or (c) defined above, in free form or in salt or complex form.

These novel compounds can be prepared as described above for the compounds according to the invention. The present invention also comprises the corresponding process for the production of the novel compounds.

What we claim is:

1. A compound of formula I

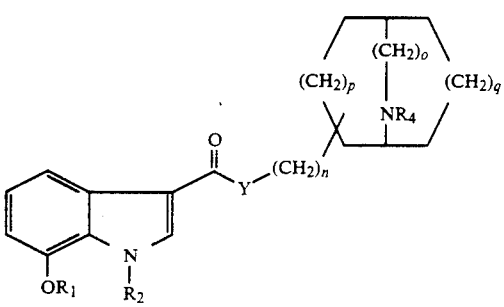

I wherein
$R_1$ is $C_{1-4}$alkyl;
$R_2$ is hydrogen, $(C_{1-7})$alkyl, $(C_{3-6})$alkenyl, $(C_{3-10})$alkynyl, $(C_{3-7})$cycloalkyl, $(C_{3-7})$cycloalkyl$(C_{1-4})$alkyl, phenyl, phenyl$(C_{1-3})$alkyl, $(C_{1-6})$alkylcarbonyl, $(C_{1-6})$alkoxycarbonyl, carbamoyl, sufamoyl, or mono- or di-$(C_{1-6})$alkyl substituted carbamoyl or sulfamoyl;
Y is O or $NR_3$, where $R_3$ is hydrogen or $(C_{1-6})$alkyl;
n is 0, 1 or 2;
$R_4$ is hydrogen, $(C_{1-7})$alkyl, $(C_{3-6})$cycloalkyl, phenyl$(C_{1-4})$alkyl, or phenyl$(C_{1-4})$alkyl mono- or disubstituted by halo, $(C_{1-4})$alkyl or $(C_{1-4})$alkoxy; and
o is 0, p is 1 and q is 0,
or
o is 1, p is 0 and q is 0;
in free base or pharmaceutically acceptable salt or complex form.

2. A compound of claim 1 wherein $R_1$ is $(C_{1-4})$alkyl; $R_2$ is hydrogen, Y is O or NH, n is 0, $R_4$ is methyl, ethyl or propyl, o is 0, p is 1 and q is 0 and the indole carboxylic acid or amide moiety is attached to the 3-position of the azabicyclo-octyl ring, in free base or pharmaceutically acceptable salt or complex form.

3. A compound which is 7-methoxy-1H-indol-3-carboxylic acid-(1αH, 5αH)-8-methyl-8-aza-bicyclo[3,2,1]-oct-3α-yl-ester, in free base or pharmaceutically acceptable salt or complex form.

4. A pharmaceutical composition useful in treating anxiety comprising a pharamaceutically acceptable carrier or diluent and a therapeutically effective amount of a compound of claim 1, in free base or pharmaceutically acceptable salt or complex form.

5. A method of treating anxiety comprising administering to a subject in need of such treatment a therapeutically effective amount of a compound of claim 1, in free base or pharmaceutically acceptable salt or complex form.

* * * * *